(12) United States Patent
Chinyere et al.

(10) Patent No.: US 10,856,938 B2
(45) Date of Patent: Dec. 8, 2020

(54) CARDIAC ELECTROPHYSIOLOGIC MAPPING AND STIMULATION

(71) Applicant: THE ARIZONA BOARD OF REGENTS ON BEHALF OF THE UNIVERSITY OF ARIZONA, Tucson, AZ (US)

(72) Inventors: Ikeotunye Royal Chinyere, Tucson, AZ (US); Jen Watson Koevary, Tucson, AZ (US); Jordan Lancaster, Tucson, AZ (US); Steven Goldman, Tucson, AZ (US); Russell Witte, Tucson, AZ (US); Kyle Weigand, Tucson, AZ (US)

(73) Assignee: THE ARIZONA BOARD OF REGENTS ON BEHAFT OF THE UNIVERSITY OF ARIZONA, Tucson, AZ (US)

(*) Notice: Subject to any disclaimer, the term of this patent is extended or adjusted under 35 U.S.C. 154(b) by 158 days.

(21) Appl. No.: 16/028,020

(22) Filed: Jul. 5, 2018

(65) Prior Publication Data
US 2019/0008584 A1 Jan. 10, 2019

Related U.S. Application Data

(60) Provisional application No. 62/529,177, filed on Jul. 6, 2017.

(51) Int. Cl.
A61B 18/14 (2006.01)
A61B 5/0464 (2006.01)
(Continued)

(52) U.S. Cl.
CPC ........ *A61B 18/1492* (2013.01); *A61B 5/0422* (2013.01); *A61B 5/0464* (2013.01);
(Continued)

(58) Field of Classification Search
USPC .......................................... 600/509
See application file for complete search history.

(56) References Cited

U.S. PATENT DOCUMENTS

2011/0230775 A1* 9/2011 Barley ............... A61B 5/02007
600/508

* cited by examiner

*Primary Examiner* — Amanda K Hulbert
*Assistant Examiner* — Philip C Edwards
(74) *Attorney, Agent, or Firm* — Lathrop GPM LLP

(57) ABSTRACT

Systems are provided for assessing the likelihood that a sample of cardiac tissue will spontaneously exhibit disordered electrical activity. These systems induce ventricular tachycardia or other disordered electrical activity in a sample of human and/or animal cardiac tissue either in vivo or in vitro. This system can be used to assess the ability of various pharmaceuticals, genetic modifications, electrical pacing, surgical ablation, or other therapeutic interventions to prevent or halt such disordered electrical activity. This system detects electrical activity from a plurality of points on the surface of the sample of cardiac tissue and generates one or more maps of monophasic action potential amplitude, monophasic action potential duration, local field amplitude, or other electrophysiological parameters of the cardiac tissue. These maps are then used to assess the likelihood that the sample will spontaneously exhibit disordered electrical activity and/or to assess the effect of a therapeutic intervention on that likelihood.

20 Claims, 4 Drawing Sheets

(51) Int. Cl.
*A61B 5/042* (2006.01)
*A61B 5/00* (2006.01)
*A61B 18/00* (2006.01)

(52) U.S. Cl.
CPC .......... *A61B 5/7275* (2013.01); *A61B 5/4848* (2013.01); *A61B 2018/0016* (2013.01); *A61B 2018/00273* (2013.01); *A61B 2018/00351* (2013.01); *A61B 2018/00577* (2013.01); *A61B 2018/00839* (2013.01); *A61B 2018/1465* (2013.01)

CARDIAC ELECTROPHYSIOLOGIC MAPPING AND STIMULATION

CROSS-REFERENCE TO RELATED APPLICATION

This application claims priority to U.S. Provisional Patent Application No. 62/529,177, filed Jul. 6, 2017, which is incorporated herein by reference.

BACKGROUND

In the United States, one in three deaths is attributed to cardiovascular disease (CVD). Within CVD, sudden cardiac death (SCD) is an increasingly common cause of mortality. Patients with prior myocardial infarction and subsequent ischemic cardiomyopathy are at risk of developing ventricular tachycardia (VT) and/or fibrillation leading to SCD.

SUMMARY

An aspect of the present disclosure relates to a method for determining likelihood that cardiac tissue will exhibit disordered electrical activity, the method including: (i) providing, prior to a first period of time, an electrical stimulus to a first sample of cardiac tissue, wherein the electrical stimulus is specified to induce tachycardia in damaged or genetically-altered cardiac tissue; (ii) detecting, during the first period of time, a plurality of electrical signals, wherein each electrical signal in the plurality of electrical signals is detected from a respective point on a surface of the first sample; (iii) determining a first plurality of physiological parameters for the first sample, wherein each parameter in the first plurality of physiological parameters is determined for a respective point on the surface of the first sample based on the electrical signal detected from the respective point on the surface of the first sample during the first period of time; (iv) based on the first plurality of physiological parameters, determining a first likelihood that the first sample of cardiac tissue will exhibit disordered electrical activity.

Another aspect of the present disclosure relates to a system including: (i) a plurality of electrodes configured to be applied to a sample of cardiac tissue; (ii) at least one stimulation electrode configured to apply stimulus to the sample of cardiac tissue; and (iii) a controller operably coupled to the plurality of electrodes and to the at least one stimulation electrode. The controller includes at least one processor programmed to perform controller operations including: (a) providing, prior to a first period of time, an electrical stimulus via the at least one stimulation electrode to the first sample of cardiac tissue, wherein the electrical stimulus is specified to induce tachycardia in damaged or genetically-altered cardiac tissue; (b) detecting, during the first period of time, a plurality of electrical signals via the plurality of electrodes, wherein each electrical signal in the plurality of electrical signals is detected from a respective point on a surface of the first sample; (c) determining a first plurality of physiological parameters for the first sample, wherein each parameter in the first plurality of physiological parameters is determined for a respective point on the surface of the first sample based on the electrical signal detected from the respective point on the surface of the first sample during the first period of time; and (d) based on the first plurality of physiological parameters, determining a first likelihood that the first sample of cardiac tissue will exhibit disordered electrical activity.

Yet another aspect of the present disclosure relates to an electrode array including: (i) a flexible substrate; (ii) a first plurality of surface electrodes disposed on the flexible substrate according to a first electrode spacing; (iii) a second plurality of penetrating electrodes disposed on the flexible substrate according to a second electrode spacing, wherein the second electrode spacing is less than the first electrode spacing; and (iv) at least one stimulating electrode disposed on the flexible substrate.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

DETAILED DESCRIPTION

Figure 1:
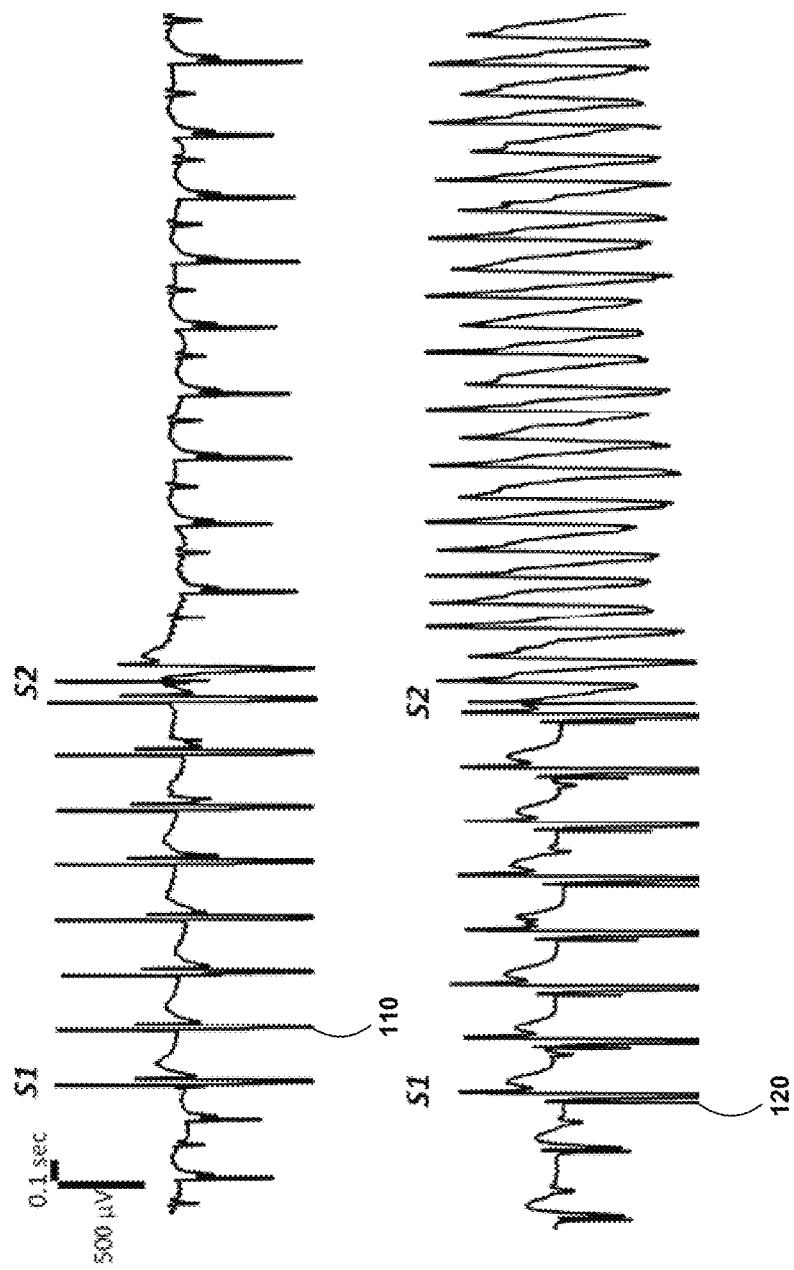
FIG. 1 depicts example electrophysiological signals.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. OVERVIEW

The heart can be damaged by arterial narrowing, arterial blockage, chemical substances, infection, physical trauma, or other events or conditions. Such damage may result in the development of disordered electrical activity, which may lead to further damage to the heart, reduced cardiac output, heart attack, damage to other elements of the cardiovascular system, damage to the lungs or other organs, or death. Additionally or alternatively, genetic changes in the cells of the heart or elsewhere can cause such disordered electrical activity to occur.

It can be beneficial to correct such disordered electrical activity, e.g., to increase cardiac output, to prevent the occurrence of major cardiac events (e.g., heart attacks), to improve overall cardiac health and/or to protect remaining healthy cardiac tissue, or to provide some other benefits. A variety of therapies may be applied to correct such disordered electrical activity, e.g., pharmaceuticals, surgical intervention (e.g., resection, radio-frequency ablation, application of tissue grafts), electrical pacing or other electrical stimulus, genetic therapy, or other methods.

However, it can be difficult to assess the efficacy of putative therapies, due, e.g., to the complicated system dynamics of the electrically active tissues of the heart. The systems and methods provided herein seek to provide improved assessment of therapies by providing repeatable induction of disordered electrical activity in damaged tissue and by detecting electrophysiological signals across the surface of a heart or other cardiac tissue (e.g., a cultured sample of cardiac tissue) in order to quantify the degree to which the electrical activity of the tissue is disordered. The stimulation protocols disclosed herein facilitate the consistent, repeatable induction of disordered electrical activity (e.g., tachycardia) in a sample of cardiac tissue when that sample is damaged (e.g., by ischemia, by exhibiting abnormal protein expression, by exhibiting a mutation), but not when that sample is normal or otherwise undamaged. Additionally, the signal detection and analysis techniques disclosed herein facilitate the assessment and quantification of the overall system-level effect of a proposed therapy on rectifying and/or improving the electrical and/or mechanical function of a sample of cardiac tissue. Additionally or alternatively, these methods can be used to assess the effectiveness of various experimental methods used to induce damage in cardiac tissue for the purpose of assessing treatments or for other investigative purposes. These methods can facilitate improved functional assessment of therapies with respect to functional effects on cardiac health and output.

Disordered electrical activity of the heart can include ventricular tachycardia, ventricular fibrillation, ventricular bradycardia, atrial tachycardia, atrial fibrillation, atrial bradycardia, premature atrial contraction, premature ventricular contraction, atrial flutter, extra heartbeats, torsades de pointes, heart block, or other arrhythmias or disordered patterns of electrical conduction or non-conduction within or between the tissues of the heart. Such disordered electrical activity can be caused by damage to portions of the heart. This damage can then result in changes in the electrical activity and/or connectivity of the electrically active tissues of the heart. Such changes may result in the formation of re-entrant electrical circuits within the tissue of the heart, blocked conduction between regions of the heart, slowed or speeded conduction between or within regions of the heart, inconsistent conduction between or within regions of the heart, or other deviations from normal heart tissue function that may result in disordered electrical activity.

Damaged cardiac tissue is any human or animal cardiac tissue that has been exposed to a damaging agent, injured, genetically modified, caused to exhibit abnormal protein expression, or otherwise caused to exhibit functionality that differs, with respect to a metric of tissue functionality or health, by more than a specified threshold amount relative to baseline cardiac tissue (e.g., relative to an average metric measured from healthy or otherwise normal cardiac tissue). Damaged cardiac tissue could differ with respect to cardiac output (e.g., blood flow rate, maximum blood pressure, blood volume pumped), electrical activity (e.g., a magnitude of a generated electrocardiographic signal), metabolic activity (e.g., a rate of consumption of oxygen, a rate of generation of carbon dioxide, a rate of consumption of glucose or other chemical energy sources), vascular status or activity (e.g., a degree or variability of perfusion of the cardiac tissue), or some other metric of the function, composition, or overall health of the cardiac tissue by more than a specified threshold amount, e.g., by more than 5%, more than 10%, more than 15%, more than 20%, more than 25%, more than 30%, more than 35%, more than 40%, more than 45%, more than 50%, or by more than some other specified amount relative to baseline cardiac tissue. Cardiac tissue as described herein can include human or animal cardiac tissue, and that tissue may be extracted from an animal body (e.g., as a whole heart or a volume of heart muscle removed from the body of a rat) and/or that tissue may be cultured or otherwise prepared via chemical or biological processes.

Damaged cardiac tissue can include cardiac tissue that has experienced periods of hypoxia or that has otherwise accrued ischemic damage. Damaged cardiac tissue can include cardiac tissue that has experienced physical trauma, e.g., surgical resection, exposure to high or low temperature or pressure or other extreme environments, thermal or radio frequency ablation, or other physical damage. Damaged cardiac tissue can include cardiac tissue that has been exposed to chemical, pharmaceutical, or biological agents, e.g., high or low pH solutions, infections bacteria, viruses, or other biological agents, solutions containing hormones or enzymes, or other chemical and/or biological agents. Damaged cardiac tissue can include cardiac tissue that has been genetically modified (e.g., by transfection by a retroviral agent) and/or cardiac tissue of an animal that bears a mutation (e.g., brugada, long QT syndrome) causing reduced cardiac function or some other deleterious effect on the cardiac tissue relative to wild type animals. Damaged cardiac tissue can include cardiac tissue that has been damaged by an autoimmune response.

II. EXAMPLE METHODS

Example systems and methods herein facilitate providing consistent, repeatable stimulus for the induction of abnormal electrical activity (e.g., ventricular tachycardia, electrical alternans, or some other arrhythmia or otherwise disordered electrical activity) in samples of cardiac tissue and the detection and analysis of resulting electrical activity of the cardiac tissue in order to efficiently assess the effectiveness of therapies for cardiac abnormalities (e.g., ischemic, mechanical, thermal, or other sources of tissue damage, infection, genetic mutations or abnormalities, abnormal protein expression, or other disease or damage states). These methods can be applied to assess the efficacy of various treatments and interventions in reducing abnormal electrical activity (e.g., reducing the occurrence of spontaneous ventricular tachycardia or other abnormal electrical activity) for clinical applications, to assess the efficacy of interventions for increasing and/or inducing abnormal electrical activity (e.g., to provide models of abnormal cardiac function that can be used to develop treatments and expand the understanding of disease processes in cardiac tissue), and to assess the electrical activity and health of cardiac tissue as part of basic scientific investigations.

To reliably, repeatably induce abnormal electrical activity in samples of cardiac tissue (e.g., samples of in vivo cardiac tissue that are part of an intact and/or damaged heart, samples of explanted, ex vivo cardiac tissue, samples of cardiac tissue cultured from stem cells or generated by some other method), one or more pulses of electrical stimulation can be provided to the sample of cardiac tissue. The number and timing of the pulses, the pulse amplitude and waveform, or other properties of the provided stimulation can be specified such that damaged or genetically-altered cardiac tissue exhibits tachycardia or some other abnormal electrical activity in response to receiving the stimulus. The ability of a proposed therapy (e.g., a gene therapy, a pharmaceutical, a surgical intervention, etc.) to prevent such stimulus-responsive abnormal activity, in diseased or otherwise abnormal cardiac tissue, could then be assessed using the methods described herein in order to assess the overall efficacy of the proposed therapy.

FIG. 1 shows electrocardiograms recorded from normal cardiac tissue (top, genetic wildtype) and genetically-altered cardiac tissue (bottom, tissue exhibiting upregulation of Fragile X RNA-binding protein 1, "FXR1") during and after stimulation of the samples of cardiac tissue with an example of electrical stimulus as described herein. The stimulus result in induced ventricular tachycardia in the genetically altered tissue, while the normal tissue exhibits normal electrical activity following the stimulation. The stimulation included a first set of pulses of stimulation (e.g., eight pulses of stimulation) provided according to a first inter-pulse interval (i.e., the first set of pulses of stimulation are provided at regular intervals). The timing of the first pulse of this first set of pulses is indicated in FIG. 1 as "S1." Subsequent to the first set of pulses, an additional pulse of stimulation was provided, with the inter-pulse interval between the additional pulse of stimulation and the last pulse of the first set of pulses being less than the first inter-pulse interval (i.e., the additional pulse is provided "early"). The timing of this additional pulse is indicated in FIG. 1 as "S2."

The first inter-pulse interval can be selected in a variety of ways. In some examples, it can be determined based on the baseline, un-stimulated pulse rate of the sample of cardiac tissue. For example, the inter-pulse interval, in milliseconds, could be determined as 60,000/HR, where "HR" is the detected baseline heart rate of the tissue sample (e.g., of the in vivo or explanted heart of an animal) in beats per minute. Additionally or alternatively, the applied inter-pulse interval can be within 10% of this determined value.

The amplitude of the pulses of stimulation can be determined based on the response (or lack thereof) of the sample of cardiac tissue to pulses of stimulation at a range of different amplitudes. For example, the response of the cardiac tissue to pulses of stimulation at a range of different amplitudes could be recorded and used to determine a threshold stimulus amplitude, e.g., by determining the lowest stimulation amplitude that causes a detectable or super-threshold response in the sample of cardiac tissue (e.g., that causes the sample of cardiac tissue to exhibit a traveling wave of electrical activity). An experimental stimulus amplitude could then be determined from the threshold stimulus amplitude and used to provide stimulus to the sample of cardiac tissue in order to induce abnormal electrical activity in the sample. This could include multiplying the threshold stimulus amplitude by a factor. Such a factor could be determined based on the species of the cardiac tissue sample and/or the type of cardiac tissue sample (e.g., in vivo, in vitro). For example, the factor could be approximately four times (e.g., between 3.8 times and 4.2 times), or greater than five times, for samples of mouse cardiac tissue. The factor could be greater than 1.5 times for samples of rat cardiac tissue. The factor could be greater than ten times for samples of cardiac tissue that comprise grafts of in vitro tissue.

In order to determine the efficacy of a therapy, or to otherwise determine whether a sample of cardiac tissue is or remains susceptible to induction of abnormal electrical activity (e.g., in response to stimulation as described herein), the electrical activity, and parameters thereof, of tissue at a plurality of points on or within the sample of cardiac tissue can be detected and analyzed. The detected activity can be electrical activity exhibited subsequent to stimulation of the sample of cardiac tissue by stimulus as described herein, e.g., to assess the electrical parameters of the tissue under conditions wherein the cardiac tissue may be exhibiting abnormal electrical activity. Performing such detection and analysis for signals spanning the tissue allows for the overall, system-level activity of the cardiac tissue sample to be assessed.

An electrical parameter may be determined, based on each electrical signal detected from the sample of cardiac tissue, for each corresponding point on or within the sample of cardiac electrical tissue. The electrical parameter may be determined based on signals from a single cell (e.g., based on a signal detected from a penetrating electrode). Such determined electrical parameters could include a characteristic myocardial action potential amplitude, a characteristic myocardial action potential duration, a determined degree of variation over time of the amplitude of myocardial action potentials (e.g., a measure of electrical alternans), or a myocardial action potential repolarization time. Additionally or alternatively, the electrical parameter may be determined based on signals from a population of cells (e.g., based on a signal detected from a large surface electrode). Such determined electrical parameters could include a characteristic unipolar electrocardiogram amplitude, a characteristic bipolar electrocardiogram amplitude, a characteristic P-wave amplitude, a characteristic P-R interval, a characteristic R-S or QRS complex width, or a characteristic Q-T interval.

These determined electrical parameters can be used to determine whether the sample of cardiac tissue is likely to exhibit disordered electrical activity, e.g., whether the sample of cardiac tissue is likely to spontaneously and/or in response to a particular stimulus exhibit one or more of ventricular fibrillation, ventricular tachycardia, atrial tachycardia, atrial fibrillation, electrical alternans, mechanical alternans, or pulseless electrical activity. Such a determination could be made based on one or more pluralities of physiological parameters determined for locations on or within the sample of cardiac tissue based on electrical signals detected from the locations on or within the sample of cardiac tissue, as described herein.

Such a determination could include determining an amount of damage present in the sample of cardiac tissue. Determining the amount of damage present in the sample of cardiac tissue can include determining, for each physiological parameter determined for a respective point on or within the sample of cardiac tissue, whether the corresponding point on or within the sample of cardiac tissue is damaged. Such a determination could include determining whether the determined physiological value has a value within a range of values that corresponds to non-damaged tissue and/or to a range of values that corresponds to tissue that is damaged in a particular way and/or damaged to a particular degree.

For example, in rat cardiac tissue that has experienced ischemic damage, healthy tissue exhibits parameter values within the ranges of 9.5588 to 25.4173 millivolts for action potential amplitudes, 35.5 to 42.3 milliseconds for 90% repolarization time, 3.15567 to 17.0057 millivolts for bipolar electrocardiogram amplitudes, and 5.4596 to 22.733 millivolts for unipolar electrocardiogram amplitudes (ranges expressed for fifth percentile to ninety-fifth percentile for healthy tissue). In rat cardiac tissue that has experienced ischemic damage, tissue on the border between healthy and scarred tissue exhibits parameter values within the ranges of 6.968 to 9.5587 millivolts for action potential amplitudes, 42.4 to 53.7 milliseconds for 90% repolarization time, 1.39258 to 3.15566 millivolts for bipolar electrocardiogram amplitudes, and 3.31405 to 5.4595 millivolts for unipolar electrocardiogram amplitudes (ranges expressed for fifth percentile to ninety-fifth percentile for border tissue). In rat cardiac tissue that has experienced ischemic damage, scarred tissue exhibits parameter values within the ranges of 0.303988 to 6.967 millivolts for action potential amplitudes, 53.8 to 100 milliseconds for 90% repolarization time, 0.0229288 to 1.39257 millivolts for bipolar electrocardiogram amplitudes, and 0.089304 to 3.31404 millivolts for unipolar electrocardiogram amplitudes (ranges expressed for fifth percentile to ninety-fifth percentile for border tissue).

Additionally or alternatively, determining whether the sample of cardiac tissue is likely to exhibit disordered electrical activity can include generating a map of the determined physiological parameters for the sample of cardiac tissue. Such a map can then be used, by human inspection and/or by application of further analysis, to determine whether the sample of cardiac tissue is likely to exhibit disordered electrical activity. Such a map can be generated by normalizing a plurality of physiological parameters determined for the sample of cardiac tissue and then generating the map based on the normalized parameters. The map can be used to determine whether the sample of cardiac tissue is likely to exhibit disordered electrical activity by determining a level of heterogeneity of the physiological parameters within the map (e.g., by determining a standard deviation of the physiological parameters within the map and comparing the determined standard deviation to a threshold value) and/or by detecting the presence or absence of a specified pattern within the map, e.g., by detecting the presence of gradients, lines of damage, points of damage, or other features within the map.

Figure 2A:
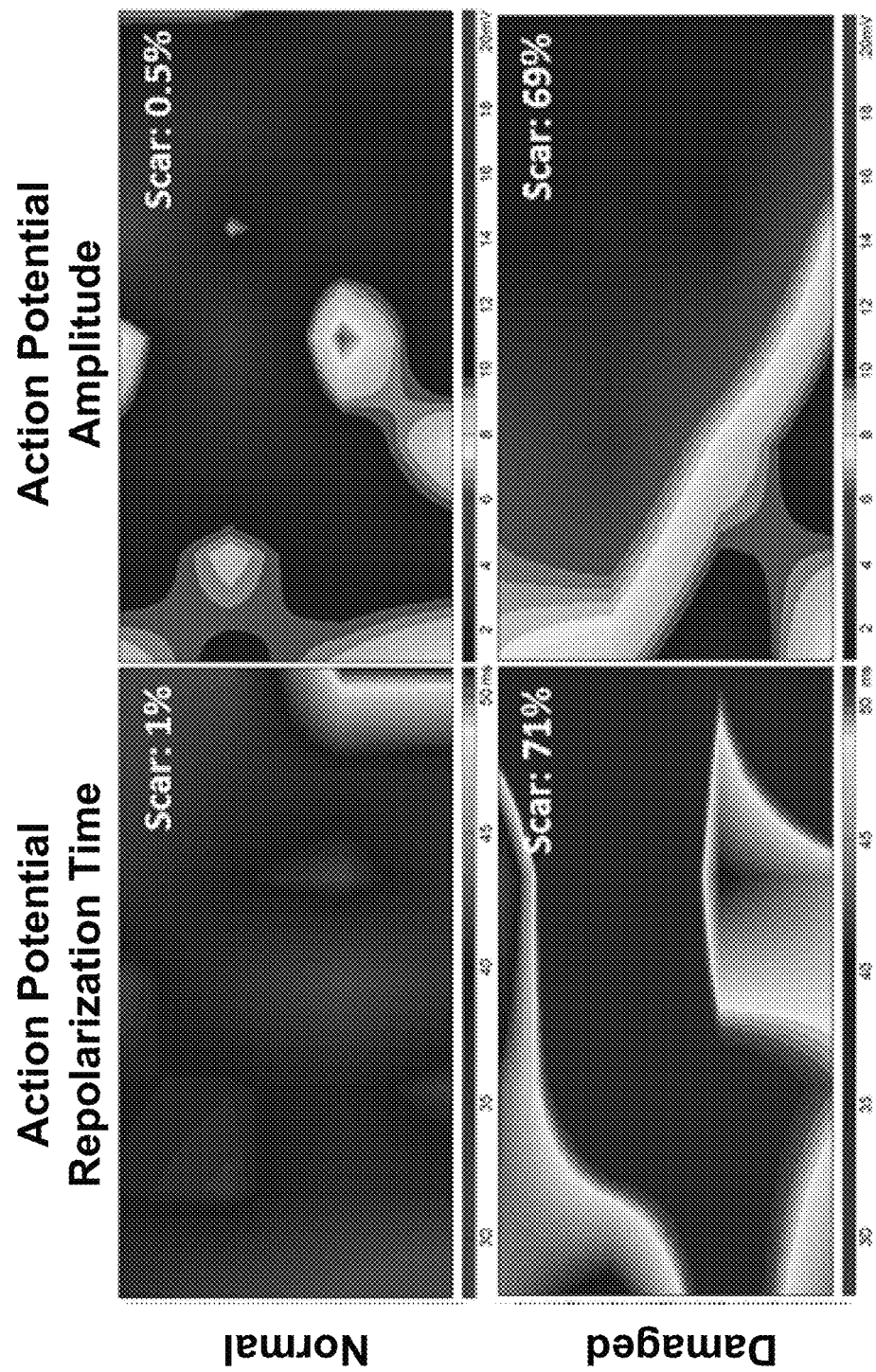
FIG. 2A depicts experimentally-observed maps of electrophysiological parameters determined for a cardiac tissue sample.
Figure 2B:
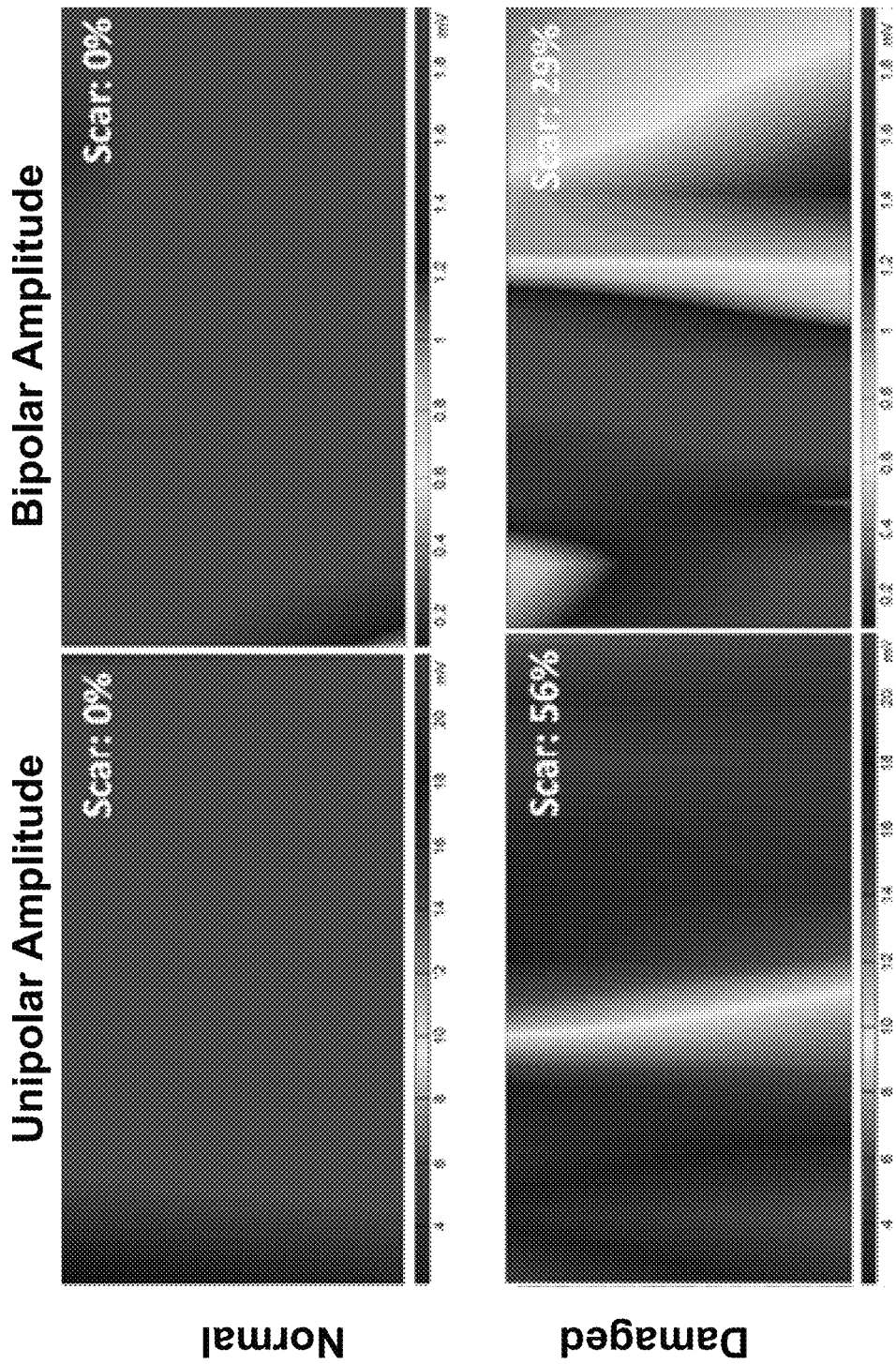
FIG. 2B depicts experimentally-observed maps of electrophysiological parameters determined for a cardiac tissue sample.

FIGS. 2A and 2B show example maps determined for a normal sample of cardiac tissue (above) and a sample of cardiac tissue that has experienced ischemic damage (below). FIG. 2A shows color-coded maps of action potential repolarization time (left) and action potential amplitude (right), and FIG. 2B shows color-coded maps of unipolar electrocardiogram amplitude (left) and bipolar electrocardiogram amplitude (right). The physiological parameters used to generate these maps can also be used to determine an amount of the cardiac tissue that is damaged, e.g., by comparing the physiological parameter values to specified ranges of values as described above. This is illustrated in FIGS. 2A and 2B by the indicated "Scar" percent damage values for each sub-plot.

The likelihood that multiple samples of cardiac tissue will exhibit disordered electrical activity and/or the likelihood that a single sample of cardiac tissue will exhibit disordered electrical activity at different points in time (e.g., points in time before and after administration of a putative therapy) can be determined, based on multiple different time periods and corresponding detected electrical signals, in order to determine the efficacy of a drug, surgical intervention, genetic therapy, or other treatment. Additionally or alternatively, these methods can be used to assess the effectiveness of laboratory interventions intended to induce damage, genetic mutations, or other interventions in samples of cardiac tissue to facilitate assessment of potential therapies, to investigate the mechanisms function and dysfunction of cardiac tissue, or to provide some other benefit.

In another example, the methods described herein can be used to determine a first likelihood that a sample of cardiac tissue will exhibit disordered electrical activity for a first period of time. Subsequent to the first period of time, the sample of cardiac tissue can be subjected to a therapeutic intervention. The therapeutic intervention could include exposing the sample of tissue to a pharmaceutical (e.g., by administering the pharmaceutical to the bloodstream of an animal that includes the tissue under study, by adding the pharmaceutical to a nutrient bath or perfusate to which an in vitro tissue sample is exposed), subjecting the tissue sample to physical resection and/or radio frequency ablation, exposing the tissue sample to a gene therapy (e.g., applying a sample of an infectious agent tailored to induce a genetic change in cells of the tissue), subjecting the tissue sample to electrical pacing or some other artificial input, applying a tissue graft or other sample of cultured or otherwise obtained cells or tissue to the tissue sample, stenting or otherwise manipulating vasculature of the tissue sample, or applying some other intervention. A second likelihood that the sample of cardiac tissue will exhibit disordered electrical activity can then be determined for a second period of time that is subsequent to and/or contemporaneous with the therapeutic intervention. The first and second likelihoods can then be compared in order to assess the efficacy (e.g., the magnitude of the degree of effect) of the therapeutic intervention. Additionally, the first likelihood can be used to verify that an experimental intervention intended to induce damage, genetic change, or some other abnormality in the tissue has been effective in inducing such abnormality.

To facilitate such assessment of therapeutic interventions, the sample of cardiac tissue can be intentionally damaged, caused to exhibit abnormal genetic or protein expression, or caused to vary from healthy cardiac tissue in some other way in order to act as a model for cardiac disease or other disease processes or interest. This can include transfecting a number of animals with a genetic vector and/or breeding such animals such that they exhibit a specified genetic alteration or abnormality (e.g., such that they exhibit Fragile X cardiomyopathy and/or exhibit Fragile X RNA-binding protein 1 (FXR1) upregulation). In another example, animals may be subjected to a surgical intervention, e.g., radio frequency ablation of tissue, surgical resection or debridement of tissue, exposure of tissue to hot or cold temperatures, induced ischemia (e.g., by left coronary artery ligation), or other surgical interventions. These various interventions may be tailored in order to provide models for a variety of clinical conditions, e.g., cardiomyopathy, arrhythmogenic right ventricular dysplasia, ventricular tachycardia, spontaneous ventricular fibrillation, cardiac infarction, or other maladies of interest.

In examples wherein the same sample of cardiac tissue is assessed before and after a therapeutic intervention, laboratory intervention (e.g., to induce damage in the tissue sample), or some other event by the same system in order generate both the first and second likelihoods, a user interface of the system can be operated to provide an indication that the therapeutic intervention has been provided to the sample of cardiac tissue. An electrical stimulus can then be provided to the sample of cardiac tissue, responsive to the indication, in order to generate the second likelihood.

III. EXAMPLE ELECTRODE ARRAYS

As described above, the methods herein include detecting a plurality of electrophysiological signals from a corresponding plurality of different points across a surface of a sample of cardiac tissue (e.g., a heart in place within the body of a human, mouse, or other animal, an explanted sample of cardiac tissue, a cultured sample of cardiac tissue). In order to access such signals, an electrode array may be provided and applied to the sample of cardiac tissue. Such an electrode array may include electrodes for accessing signals related to populations of cardiac cells (e.g., surface electrodes for accessing unipolar and/or bipolar electrocardiograms) and/or electrodes for accessing signals related to individual cardiac cells (e.g., penetrating electrodes for accessing single-cell transmembrane voltages).

Such an electrode array may include a flexible substrate on and/or in which are disposed a plurality of electrodes. The flexible substrate may be composed of a hydrophilic polymer (e.g., to encourage adhesion between the substrate and a sample of cardiac tissue). The electrodes may be disposed on a surface of the flexible substrate (e.g., by being adhered to the substrate via an adhesive or other method, by being formed on the substrate via sputtering or some other method) and/or disposed partially within the substrate (e.g., by forming the substrate via injection molding or some other process such that the electrodes are partially embedded within the formed substrate). Wires or other conductors electrically connected to the electrodes may be routed on/through the substrate and/or formed on the substrate (e.g., via a process of sputtering followed by pattern formation using resist masks). The flexible substrate may include an array of slots, holes, or other features to increase the flexibility of the overall electrode array and/or to allow the electrode array to be elastically deformed in order to promote conformation to the surface of a sample of cardiac tissue.

The electrodes of the electrode array may have a variety of shapes. Non-penetrating electrodes may be flat circular electrodes or other flat shapes formed and/or disposed on a surface of the flexible substrate and composed of an appropriate material (e.g., gold, silver, silver chloride). Non-penetrating electrodes may have a diameter or other characteristic size that is between 10 millimeters and 2 centimeters, according to the characteristics of the cardiac tissue under investigation. Penetrating electrodes may be composed of wire (e.g., square or otherwise shaped wire with, e.g., a sharpened tip to encourage penetration of a sample of cardiac tissue) or material shaped to penetrate tissue (e.g., cone-shaped elements formed via machining, molding, or some other process out of metal or some other appropriate material). Penetrating electrodes may have a height specified to penetrate cardiac tissue sufficiently to access electrical signals of interest, e.g., a height of between 50 millimeters and 10 millimeters.

Figure 3:
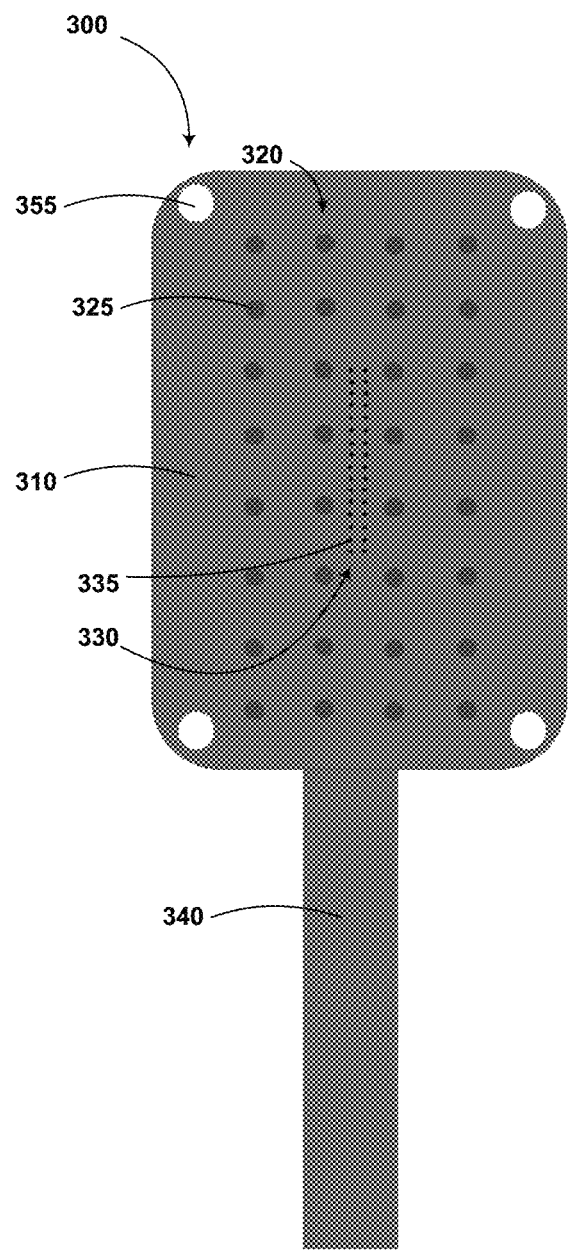
FIG. 3 depicts a schematic of an example electrode array.

An electrode array may include both penetrating and non-penetrating electrodes. This is illustrated in FIG. 3, which shows an example electrode array 300. The electrode array 300 includes a flexible substrate 310. A first plurality of non-penetrating electrodes 320 (including example non-penetrating electrode 325) and a second plurality of penetrating electrodes 330 (including example penetrating electrode 335) are disposed on a surface of the flexible substrate 310 such that the first 320 and second 330 pluralities of electrodes can access respective sets of electrophysiological signals from a sample of cardiac tissue with the electrode array 300 is applied to the sample of cardiac tissue.

The first 320 and second 330 pluralities of electrodes have respective different electrode spacings (e.g., respective different electrode areal densities and/or inter-electrode distances). Correspondingly, the two pluralities of electrodes 320, 330 span respective different total areas of the flexible substrate. For example, the plurality of electrodes having the lesser electrode spacing (e.g., the second plurality of electrodes 330) may span an area that is less than $1/16^{th}$ of the area spanned by the plurality of electrodes having the greater electrode spacing. As shown, the second plurality of electrodes 330 (having the lesser electrode spacing) is located near the center of the first plurality of electrodes 320.

The electrode array 300 additionally includes a lead 340 containing electrical conductors (e.g., wires, conductive traces formed on a surface of the flexible substrate 310) to facilitate connection between the electrodes 320, 330 and amplifiers or other electrical equipment.

While FIG. 3 illustrates an electrode array having two pluralities of electrodes arranged according to a square grid, electrodes of such an array may be arranged according to a hexagonal grid, a triangular grid, or according to some other regular or irregular pattern. Further, the illustrated number of electrodes and/or number of rows/columns of electrodes are intended as a non-limiting example embodiment. An electrode array as described herein may include more or fewer electrodes arranged in more or fewer columns/rows.

The electrode array 300 includes holes (including example hole 355) disposed at the edges/corners of the array 300. Such holes may be provided to facilitate the use of sutures, glues, or other means to adhere and/or secure the electrode array 300 to a sample of cardiac tissue.

An electrode array as described herein (e.g., 300) may also include electrodes configured to provide a stimulus to a sample of cardiac tissue (e.g., a stimulus configured to induce ventricular tachycardia or other abnormal electrical activity in damaged, diseased, or otherwise abnormal cardiac tissue). Such stimulation electrodes may be disposed at the center of such an electrode array and/or at the edges of such an array. For example, the electrode array 300 could include one or more stimulating electrodes (not shown) disposed at the center of the electrode array 300 (e.g., near or within the second plurality of electrodes 330) and/or at the edges of the electrode array 300 (e.g., near each of the holes at the corners of the electrode array 300).

VI. CONCLUSION

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:

1. A method for determining likelihood that cardiac tissue will exhibit disordered electrical activity, comprising:
   providing, prior to a first period of time, an electrical stimulus to a first sample of cardiac tissue, wherein the electrical stimulus is specified to induce tachycardia in damaged or genetically-altered cardiac tissue, and wherein providing the electrical stimulus to the first sample of cardiac tissue comprises at least one of:
   (i) providing eight repeated pulses of stimulation according to a first inter-pulse interval and providing a ninth pulse of stimulation subsequent to the eight repeated pulses of stimulation, wherein an inter-pulse interval between the last stimulation pulse of the eight repeated pulses of stimulation and the ninth pulse of stimulation is less than the first inter-pulse interval; or
   (ii) applying an electrical stimulus at an experimental stimulus amplitude to the first sample of cardiac tissue, wherein the experimental stimulus amplitude is between one-and-a-half times a threshold stimulus amplitude and ten times the threshold stimulus amplitude, wherein the threshold stimulus amplitude is sufficient, when applied to the first sample of cardiac tissue, to induce a wave of electrical activity in the first sample of cardiac tissue;
   detecting, during the first period of time, a plurality of electrical signals, wherein each electrical signal in the plurality of electrical signals is detected from a respective point on a surface of the first sample;
   determining a first plurality of physiological parameters for the first sample, wherein each parameter in the first plurality of physiological parameters is determined for a respective point on the surface of the first sample based on the electrical signal detected from the respective point on the surface of the first sample during the first period of time;
   based on the first plurality of physiological parameters, determining a first likelihood that the first sample of cardiac tissue will exhibit disordered electrical activity.

2. The method of claim 1, further comprising:
   generating, based on the determined first plurality of physiological parameters, a first map of the first sample, wherein determining a first likelihood that the first sample of cardiac tissue will spontaneously exhibit disordered electrical activity comprises determining the first likelihood based on the first map.

3. The method of claim 2, wherein generating the first map of the first sample comprises:
   normalizing the first plurality of physiological parameters for the first sample; and
   generating the first map of the first sample based on the normalized first plurality of physiological parameters.

4. The method of claim 2, wherein determining a first likelihood that the first sample of cardiac tissue will spontaneously exhibit disordered electrical activity comprises detecting the presence of a specified pattern within the first map.

5. The method of claim 1, wherein the first sample of cardiac tissue is a sample of tissue including but not limited to stem-cell-derived tissue, human-derived tissue, bovine-derived tissue, primate-derived tissue, canine-derived tissue, rodent-derived tissue, or murine-derived tissue, wherein the operations further comprise:
   applying a plurality of electrical stimuli, having respective different amplitudes, to the first sample of cardiac tissue;
   detecting a response of the first sample of cardiac tissue to each of the applied electrical stimuli;
   determining the threshold stimulus amplitude based on the amplitudes of the applied electrical stimuli and the detected response of the first sample of cardiac tissue; and
   determining the experimental stimulus amplitude based on the threshold stimulus amplitude, wherein providing, prior to the first period of time, the electrical stimulus to the first sample of cardiac tissue comprises applying an electrical stimulus at the experimental stimulus amplitude to the first sample of cardiac tissue.

6. The method of claim 5, wherein determining the experimental stimulus amplitude comprises determining an experimental stimulus amplitude that is between 3.8 times the determined threshold stimulus amplitude and 4.2 times the determined threshold stimulus amplitude.

7. The method of claim 1, further comprising:
   determining a second plurality of physiological parameters for the first sample, wherein each parameter in the second plurality of physiological parameters is determined for a respective point on the surface of the first sample based on the electrical signal detected from the respective point on the surface of the first sample, wherein determining a first likelihood that the first sample of cardiac tissue will spontaneously exhibit disordered electrical activity comprises determining the first likelihood based on the first plurality of physiological parameters and the second plurality of physiological parameters.

8. The method of claim 1, further comprising:
providing, prior to a second period of time, a second electrical stimulus to a second sample of cardiac tissue, wherein the second electrical stimulus is specified to induce tachycardia in damaged cardiac tissue, wherein the second sample has been subjected to a therapeutic intervention;
detecting, during the second period of time, a second plurality of electrical signals, wherein each electrical signal in the second plurality of electrical signals is detected from a respective point on a surface of the second sample;
determining a second plurality of physiological parameters for the second sample, wherein each parameter in the second plurality of physiological parameters is determined for a respective point on the surface of the second sample based on the electrical signal detected from the respective point on the surface of the second sample during the second period of time;
based on the second plurality of physiological parameters, determining a second likelihood that the second sample of cardiac tissue will spontaneously exhibit disordered electrical activity.

9. The method of claim 8, wherein the first sample of cardiac tissue and the second sample of cardiac tissue are the same sample of cardiac tissue, the method further comprising:
operating a user interface to receive a user input, wherein the user input is indicative of the sample of cardiac tissue having been subjected to the therapeutic intervention, wherein the second period of time is subsequent to a time during which the user input is received, and wherein the second electrical stimulus is provided to the sample of cardiac tissue in response to receiving the user input.

10. The method of claim 1, wherein determining a first likelihood that the first sample of cardiac tissue will spontaneously exhibit disordered electrical activity comprises determining an amount of damage present in the first sample of cardiac tissue.

11. The method of claim 10, wherein determining an amount of damage present in the first sample of cardiac tissue comprises determining, for each physiological parameter of the first plurality of physiological parameters, whether tissue at the corresponding point on the surface of the first sample is damaged.

12. The method of claim 11, wherein determining, for each physiological parameter of the first plurality of physiological parameters, whether tissue at the corresponding point on the surface of the first sample is damaged comprises determining whether each physiological parameter of the first plurality of physiological parameters has a value within a specified range of values that correspond to non-damaged tissue.

13. The method of claim 1, wherein determining a first likelihood that the first sample of cardiac tissue will spontaneously exhibit disordered electrical activity comprises determining a likelihood that the first sample of cardiac tissue will spontaneously exhibit ventricular fibrillation.

14. The method of claim 1, wherein determining a first likelihood that the first sample of cardiac tissue will spontaneously exhibit disordered electrical activity comprises determining a likelihood that the first sample of cardiac tissue will spontaneously exhibit one or more of ventricular tachycardia, atrial tachycardia, atrial fibrillation, electrical alternans, mechanical alternans, or pulseless electrical activity.

15. The method of claim 1, wherein determining a first likelihood that the first sample of cardiac tissue will exhibit disordered electrical activity comprises determining that more than a threshold number of physiological parameters of the first plurality of physiological parameters have values outside a specified range of values.

16. The method of claim 1, wherein the first plurality of physiological parameters for the first sample comprises at least one of a plurality of characteristic myocardial action potential amplitudes, a plurality of characteristic myocardial action potential durations, a plurality of determined degrees of variation over time of the amplitude of myocardial action potentials, or a plurality of characteristic myocardial action potential repolarization times.

17. The method of claim 1, wherein the first plurality of physiological parameters for the first sample comprises at least one of a plurality of characteristic unipolar electrocardiogram amplitudes, a plurality of characteristic bipolar electrocardiogram amplitudes, a plurality of characteristic P-wave amplitudes, a plurality of characteristic P-R intervals, a plurality of characteristic R-S or QRS complex widths, or a plurality of characteristic Q-T intervals.

18. A system comprising:
a plurality of electrodes configured to be applied to a sample of cardiac tissue;
at least one stimulation electrode configured to apply stimulus to the sample of cardiac tissue; and
a controller operably coupled to the plurality of electrodes and to the at least one stimulation electrode, wherein the controller comprises at least one processor programmed to perform controller operations comprising:
providing, prior to a first period of time, an electrical stimulus via the at least one stimulation electrode to the first sample of cardiac tissue, wherein the electrical stimulus is specified to induce tachycardia in damaged or genetically-altered cardiac tissue, and wherein providing the electrical stimulus to the first sample of cardiac tissue comprises providing eight repeated pulses of stimulation according to a first inter-pulse interval and providing a ninth pulse of stimulation subsequent to the eight repeated pulses of stimulation, wherein an inter-pulse interval between the last stimulation pulse of the eight repeated pulses of stimulation and the ninth pulse of stimulation is less than the first inter-pulse interval;
detecting, during the first period of time, a plurality of electrical signals via the plurality of electrodes, wherein each electrical signal in the plurality of electrical signals is detected from a respective point on a surface of the first sample;
determining a first plurality of physiological parameters for the first sample, wherein each parameter in the first plurality of physiological parameters is determined for a respective point on the surface of the first sample based on the electrical signal detected from the respective point on the surface of the first sample during the first period of time;
based on the first plurality of physiological parameters, determining a first likelihood that the first sample of cardiac tissue will exhibit disordered electrical activity.

19. A system comprising:
a plurality of electrodes configured to be applied to a sample of cardiac tissue, wherein the first sample of cardiac tissue is a sample of tissue including but not limited to stem-cell-derived tissue, human-derived tissue, bovine-derived tissue, primate-derived tissue, canine-derived tissue, rodent-derived tissue, or murine-derived tissue;

at least one stimulation electrode configured to apply stimulus to the sample of cardiac tissue; and a controller operably coupled to the plurality of electrodes and to the at least one stimulation electrode, wherein the controller comprises at least one processor programmed to perform controller operations comprising:

applying a plurality of electrical stimuli, having respective different amplitudes, to the first sample of cardiac tissue;

detecting a response of the first sample of cardiac tissue to each of the applied electrical stimuli;

determining, based on the amplitudes of the applied electrical stimuli and the detected response of the first sample of cardiac tissue, a threshold stimulus amplitude, wherein the determined threshold stimulus amplitude is sufficient, when applied to the first sample of cardiac tissue, to induce a wave of electrical activity in the first sample of cardiac tissue;

determining an experimental stimulus amplitude that is between one-and-a-half times the determined threshold stimulus amplitude and ten times the determined threshold stimulus amplitude;

providing, prior to a first period of time, an electrical stimulus via the at least one stimulation electrode to the first sample of cardiac tissue, wherein the electrical stimulus is specified to induce tachycardia in damaged or genetically-altered cardiac tissue, and wherein providing the electrical stimulus to the first sample of cardiac tissue comprises applying the electrical stimulus at the experimental stimulus amplitude to the first sample of cardiac tissue;

detecting, during the first period of time, a plurality of electrical signals via the plurality of electrodes, wherein each electrical signal in the plurality of electrical signals is detected from a respective point on a surface of the first sample;

determining a first plurality of physiological parameters for the first sample, wherein each parameter in the first plurality of physiological parameters is determined for a respective point on the surface of the first sample based on the electrical signal detected from the respective point on the surface of the first sample during the first period of time;

based on the first plurality of physiological parameters, determining a first likelihood that the first sample of cardiac tissue will exhibit disordered electrical activity.

20. The system of claim 19, wherein determining the experimental stimulus amplitude comprises determining an experimental stimulus amplitude that is between 3.8 times the determined threshold stimulus amplitude and 4.2 times the determined threshold stimulus amplitude.

* * * * *